United States Patent [19]
Göppel et al.

[11] Patent Number: 5,413,481
[45] Date of Patent: May 9, 1995

[54] METHOD AND APPARATUS FOR MANUFACTURING FITTING MEMBERS

[75] Inventors: Thomas Göppel; Susanne Neipp, both of Karlsruhe, Germany

[73] Assignee: G. Krieg, Karlsruhe, Germany

[21] Appl. No.: 57,465

[22] Filed: May 6, 1993

[30] Foreign Application Priority Data

May 6, 1992 [DE] Germany .......... 42 14 421.3

[51] Int. Cl.$^6$ .................................. A61C 9/00
[52] U.S. Cl. ........................ 433/214; 356/374
[58] Field of Search ........... 433/213, 214, 215, 223; 356/374, 376

[56] References Cited

U.S. PATENT DOCUMENTS

| | | | |
|---|---|---|---|
| 4,184,175 | 1/1980 | Mullane, Jr. | 433/215 |
| 4,663,720 | 5/1987 | Duret et al. | 433/214 |
| 4,952,149 | 8/1990 | Duret et al. | 433/215 |
| 4,964,770 | 10/1990 | Steinbichler et al. | 433/214 |

*Primary Examiner*—Cary E. O'Connor
*Attorney, Agent, or Firm*—Antonelli, Terry, Stout & Kraus

[57] ABSTRACT

For the manufacture of a fitting member, such as for a dental prosthesis, the invention proposes for the reception part receiving the same and in order to adapt to the remaining stump, a method and an apparatus in which an optical groove grating is repeatedly projected with a slight local offset onto the reception part and the photograph is used for calculating the fitting member. According to the invention the photograph of the optical groove grating projected onto the reception part takes place by means of a matrix camera for producing moiré fringes and between the optical groove grating and the reception part there is an optical deflecting device for separating the illuminating beam path impinging through the groove grating and the output beam path emanating from the reception part and recorded by the camera, the camera being a matrix camera for producing moiré fringes.

29 Claims, 3 Drawing Sheets

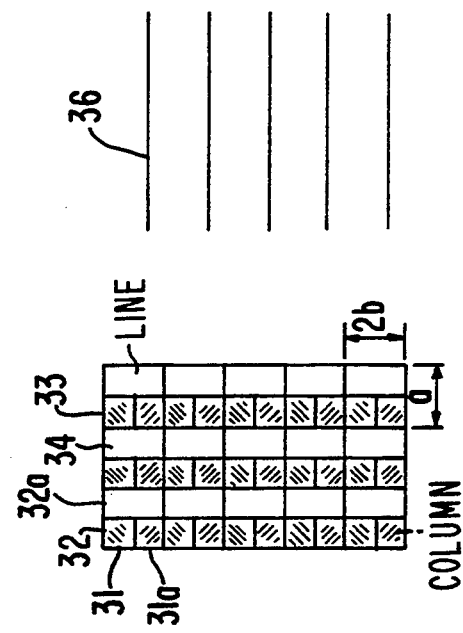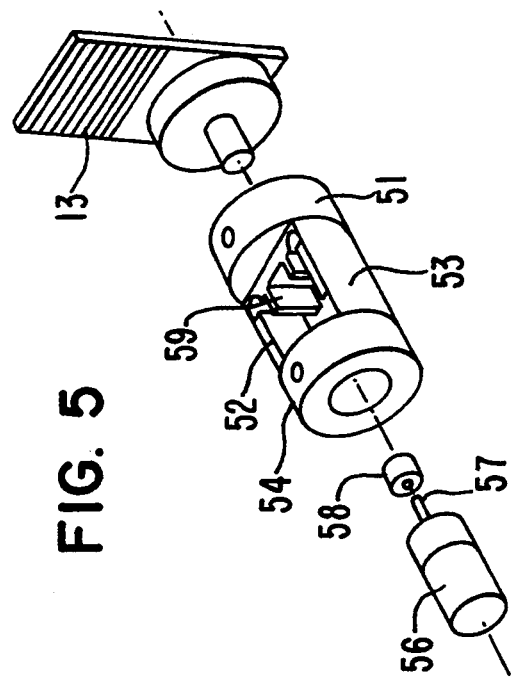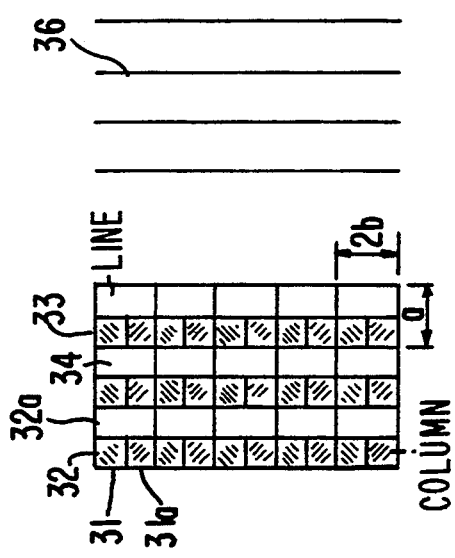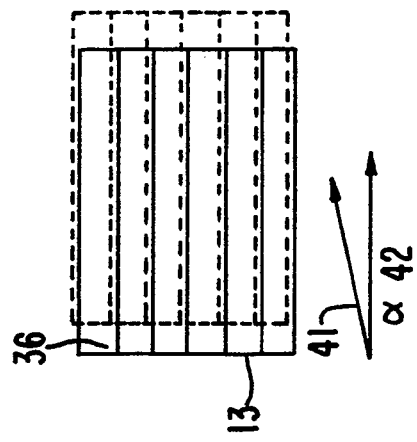

METHOD AND APPARATUS FOR MANUFACTURING FITTING MEMBERS

FIELD OF THE INVENTION

The invention relates to a method for the manufacture of a fitting member, particularly as a dental prosthesis, wherein an optical groove grating is repeatedly projected in a slightly offset manner onto a reception part for the fitting member, such as on the remaining stump, and the reception part being photographed and the photographs being used for the design calculation of the fitting member, as well as to an apparatus for the manufacture of a fitting member, such as a dental prosthesis, with an optical groove grating and an illumination system for the repeated projection of the groove grating onto a reception part for the fitting member, such as a remaining stump, and with a camera for photographing the groove grating lines of the optical groove grating projected onto the reception part.

BACKGROUND OF THE INVENTION

DE-A-3,723,555 proposes a method for the manufacture of a dental prosthesis wherein contour lines are projected by an optical groove grating onto a ground or polished stump and produce moiré contours, with the optical groove grating being photographed by a camera. At least three different contour line patterns are produced, and from the three moiré images obtained, it is possible for each camera image point or pixel to calculate the vertical coordinates on the stump and therefore the position for each point of the stump surface.

The above proposed method is complicated and requires complicated and expensive equipment and it is also not clear as to how, in practice, the method can be carried out on a stump in the mouth of a patient.

SUMMARY OF THE INVENTION

The aim of the invention is to provide an improved method and an apparatus wherein photography takes place of the optical groove grating projected onto the reception part by a matrix camera for producing moiré fringes. In an apparatus according to the invention between the optical groove grating and the reception part there is an optical deflecting device for separating the illuminating beam path impinging through the groove grating and the output beam path passing out of the reception part and photographed by the camera and that the camera is a matrix camera for producing moiré fringes.

Thus, diverging from the prior art, the invention provides that, for producing moiré structures, use is not made of the optical grating employed for projecting lines onto the stump or the reception part and there is also no observation through a second, separate optical grating. Instead the line structure of a line camera is used as a further grating for producing moiré structures. Advantageously photography takes place by means of a CCD camera.

According to a preferred development, the lines of the optical grating are optically oriented under an angle of 90° against the camera columns and in particular the photographs of the optical grating projected onto the reception part take place in the interlace mode, in which in each case fields are photographed from the columns of uneven or even numbering of the camera. Thus, the object i.e. the reception part or the remaining stump, can be photographed in image-filling manner by the camera. As a result of the interlace mode, two fields are photographed, which can be compared with one another in order to generate, in error-free manner, the measured data required for further processing.

Whereas in the prior art the projector is moved perpendicular to the projection axis or the planes defined by the grating and the illuminating beam, according to a preferred development of the invention, for repeated photography, the optical groove grating is displaced with an offset component perpendicular to the extension direction of its grooves. However, it is even then more simply and more accurately displaced than is the case for the projector.

In order to obtain a high displacement precision, according to a further development of the invention, the optical grating is displaced for offset purposes under a small angle not equal to 0 degrees against its grating lines and in particular the displacement angle against the latter is between 0.1 and 1 degree. In order to achieve the desired limited offset of the contour lines in the micrometer range with an accuracy in the nanometer range, the effective displacement of the optical groove grating can take place in the millimeter range, which is possible with an accuracy in the per mille range. This leads to a high repetition accuracy of the displacement.

There are various possibilities for the offset of the groove grating. Firstly there can be a piezoelectric offset. Generally the offset takes place substantially perpendicularly to the grating lines. However, it is disadvantageous in that high voltages are required for producing the piezoelectric effect, which are undesired in the health and medical sector. Therefore the invention alternatively proposes that the optical groove grating is moved in motor manner or that the optical groove grating is moved magnetically and in particular in the latter case the offset of the optical groove grating into the desired positions takes place by applying discrete different voltages.

A first or zero position of the optical groove grating is reproducibly achieved in that the optical grating is held in a zero position by springs relieved in said position. From said "zero position" the optical groove grating can be moved, according to a preferred development, against stops, which define two further, definitive positions.

The invention can be more particularly used for introducing a physiologically compatible masticating surface into a dental prosthesis to be produced, which allows the functional intersaction between the remaining tooth, in which the prosthesis is to be introduced, the facing teeth and the overall individual denture situation of the patient.

The data representing such a masticating surface can be generated in the following way for producing the dental prosthesis.

1. Measuring the masticating surface according to the method of the invention in a health state and using said data in the case of a defect for generating the data for the corresponding parts of the dental prosthesis.

2. Generating the approximate masticating surface from data sets, which have been obtained from generally valid rules known in dentistry and which have previously been stored.

3. In the case of minor defects measuring the masticating surface immediately prior to the preparation and use of said data for the reconstruction of the corresponding parts of the dental prosthesis.

4. Measuring the masticating surface of the lateral pendant for generating the data for the corresponding parts of the dental prosthesis using the phsiological symmetries of the human denture.

5. Introducing a plastic, health-compatible mass into the preparation and deforming the same by the patient biting and material-correct manipulation on the part of the dentist and then this provisional masticating surface is also measured.

BRIEF DESCRIPTION OF THE DRAWINGS

Further advantages and features of the invention can be gathered from the claims and the following description of a non-limitative embodiment with reference to the attached drawings, wherein:

FIG. 3a is a view of a standard arrangement of a CCD matrix.

FIG. 3b is a view of an arrangement wherein the camera is rotated by 90° relative to the optical groove grating lines.

FIG. 4 a diagrammatic representation of the displacement of the optical groove grating for producing lines on the object to be photographed for the unambiguous definition of each point of the object to be photographed in space.

FIG. 5 a diagrammatic representation of a device for displacing the optical groove grating according to FIG. 4.

DETAILED DESCRIPTION

Figure 1:
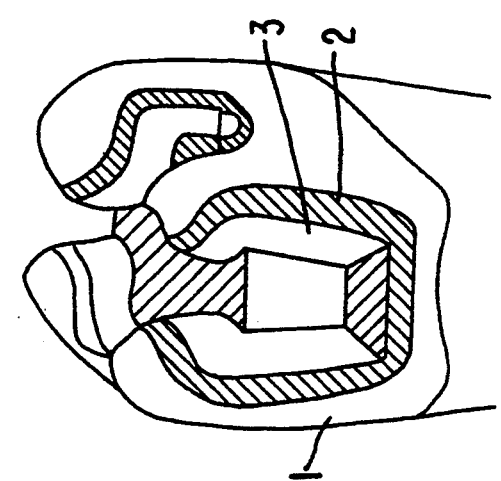
FIG. 1 a tooth prepared according to the method and apparatus according to the invention.
Figure 2:
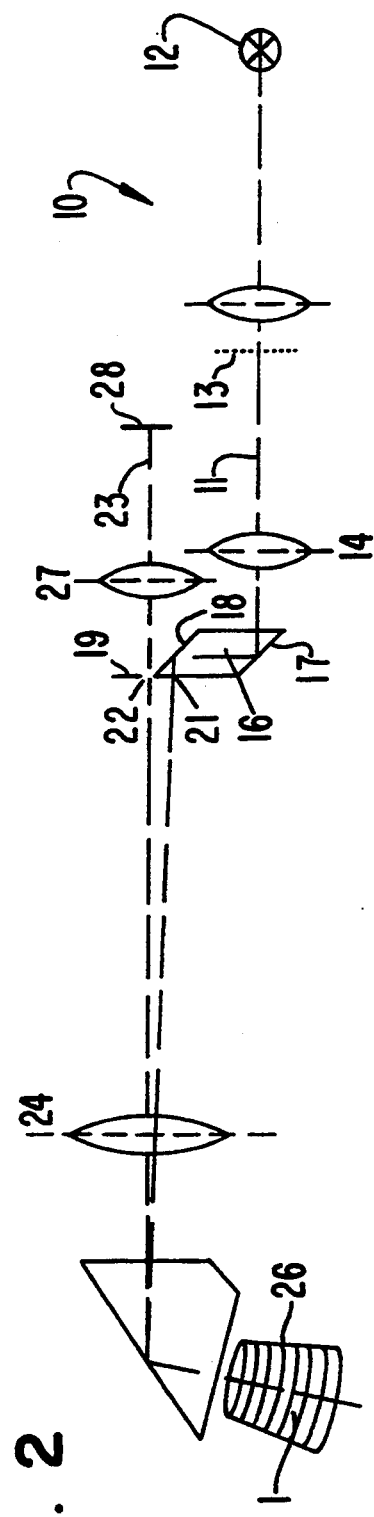
FIG. 2 the optical system of the apparatus according to the invention.

The prepared tooth 1 shown in FIG. 1 has edges 2 and faces 3, whereof on predetermining an observation direction part of the edges and faces are relatively "steep", i.e. on changing the space coordinates on a face perpendicular to the optical axis by a very small amount, the spatial modification of the point on the particular face 3 or edge 2 (particularly in a direction having a very small angle with respect to the optical arts) can be considerable. Such edges 2 or faces 3 are very difficult to determine. In conventional evaluation processes they can be looked upon as non-existing discontinuities and can therefore be incorrectly detected and not determined with an adequate degree of accuracy.

In order to permit a precise determination of a sump 1, as shown in FIG. 1, and in particular its complicated design with the indicated edges 2 and faces 3 in a highly accurate manner, the invention determines the stump 1 by using a moiré technique in the manner described hereinafter.

The apparatus generally designated by the reference numeral 10 according to the invention includes an illuminating beam path 11. The latter has an illuminating device 12, an optical groove grating 13, an imaging optics 14, a (double) prism 16 with silvered faces 17, 18 and a diaphragm 19 following the same and which, in the preferred illustrated embodiment shown, is a double diaphragm with two closely juxtaposed diaphragm apertures 21, 22. The diaphragm aperture 21 permits the passage of the illuminating beam 11, while the diaphragm aperture 22 permits the passage of an observation beam 23. The double diaphragm 19 is followed by an imaging optics 24 upstream of the stump 1 to be photographed. A groove pattern 26 is produced on the latter corresponding to the optical groove grating 13. This groove pattern is photographed by the optics 24, the diaphragm aperture 22, the double diaphragm 19, as well as a receiving optics 27 using a line camera 28.

In place of the double prism 16 with the silvered faces 17, 18 and following double diaphragm 19 with the closely juxtaposed diaphragm apertures 21, 22, it would fundamentally be possible in the conventional manner to provide half-mirrors, optionally within a prism system, in order to separate the illuminating and receiving beam paths 11, 23 on the illumination reception side and combine same on the object side (on the side of the stump 1) into a single beam path. However, in known manner, an intensity loss is linked with semisilvered mirrors and this is avoided in the system according to the invention, in which the two beams 11, 23 in a common observation and illumination head are guided by two separate, although closely juxtaposed diaphragm apertures 21, 22 of the double diaphragm 19, without it being necessary to use physically separate illuminating and observation heads. The invention also avoids the disadvantageous reflections which are unavoidable in the prior art.

Figure 6:
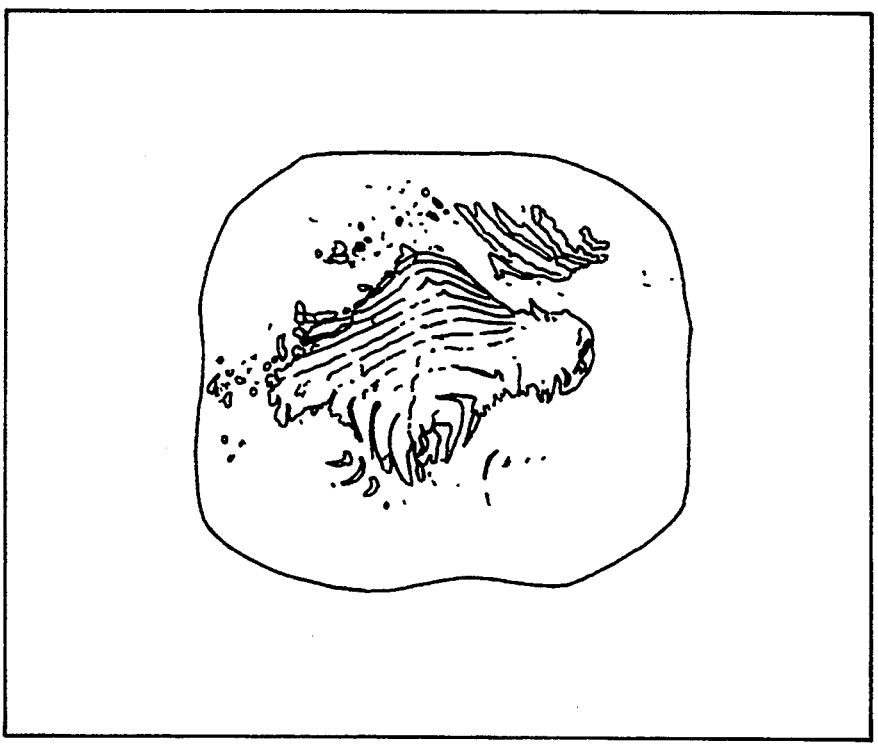
FIG. 6 moiré line photographs of a stump using the method according to the invention.

Whereas conventionally for producing moiré structures use is exclusively made of optical groove gratings (either two optical groove gratings, in each case one upstream of the illuminating system and the reception system, or optionally an optical groove grating through which pass both the illuminating beams and the reception beams), according to the invention a groove grating 13 is only introduced into the illuminating beam path 11, whereas, the further grating for forming the moiré structures is constituted by the lines 31, 31a or columns 32, 32a of the CCD matrix. A moiré photography of a prepared tooth using the method and apparatus according to the invention is shown in FIG. 6. In the case of a CCD camera between the individual light-sensitive columns 32, 32a, which are subdivided by the superimposed line structure 31, 31a into individual points 33, in each case a light-insensitive column 34 is formed in spatial-geometrical manner, in which the transposition of the charges resulting from the photography of the particular column 32 or the pixel 33 is used for the subsequent pixelwise reading.

The prepared tooth to be determined is determined with a very high lateral accuracy, which is directly dependent on the pixel resolution of the CCD camera used and naturally the size of the image of the lateral measuring area on the receiver.

Modern CCD cameras have resolutions of approximately 580×500 pixels on a photosensitive surface of 6.6 mm×8.8 mm (so-called ⅔" chips) or 4.8 mm×6.6 mm (so-called ½" chips). This leads to a smaller line height (FIG. 3, a) than column width (b).

Therefore with regards to the measuring accuracy a maximum format-filling imaging of the prepared tooth on the photosensitive CCD surface is sought. However, the projection of the optical groove grating on the tooth must, according to the invention, take place in such a way that, on considering the grooves on the tooth, the moiré effect must occur, i.e. the two grating intervals must coincide in the CCD receiver plane.

Very coarse grating structures must be sought for physicooptical reasons (e.g. diffraction effects which have a negative influence on the imaging quality). Thus, according to a preferred development, the recording surface of the CCD camera is rotated by 90° compared with the conventional arrangement, as shown in FIG. 3a, so that the lines 31, 31a, based on the optical axis of the arrangement, run parallel or in the direction of the groove lines 36 of the optical groove grating 13, whereas the columns 32, 32a are perpendicular thereto. Simultaneously, the grating constant of the optical groove grating is chosen in such a way that in the receiver plane it corresponds to the double line height of the CCD matrix.

Therefore, on reading out the CCD matrix in the standard interlaced mode (for every field alternately the even and uneven lines are read), approximately 30% coarser grating constants can be used (because $2 \times b \approx 1.3 \times a$), the lateral measuring accuracy when using both fields being improved by 40% and therefore local disturbances are less significant. In addition, the only slightly different, similar fields can be used for redundancy and plausibility purposes.

Since, according to the method of the invention, several photographs are taken of a tooth, generally three, the projection lines 26 and therefore also the lines 36 of the optical groove grating 13 being displaced by a small amount, namely a fraction of the grating constant of the optical groove grating 13, perpendicular to the lines 36, according to a further development of the invention the optical groove grating 13 is displaced in a direction 41, which forms a very small alpha of preferably 0.1 to 1° to the extension direction 42 of the groove lines 36 of the optical groove grating 13. Thus, in the case of a relatively large displacement in the direction 41 of e.g. 1 mm and which can take place with adequate accuracy, with the same percentage accuracy there can be an offset of the grating lines 36 perpendicular to their extension direction by an amount in the micrometer range. If e.g. 24 μm is assumed for the grating constant of the optical grating 13, then an offset of approximately 8 μm can be obtained. As the accuracy in the displacement direction 41 can be performed with a per mille accuracy, accuracy for the offset of the grating lines 36 is in the nanometer range.

This offset of the grating lines 36 can be achieved in different ways.

According to a preferred development a support 51 is held by leaf springs 52, 53 on the casing 54 of a motor. Through the zero position of the leaf springs 52, 53 a first, central position for the optical groove grating 13 is determined. The motor 56 has on its spindle 57 an eccentrically constructed disk 58, which engages in a slot 59 of the support 51 with a certain tolerance. In a central position of the motor the disk 58 is symmetrical to the slot 59 of the support 51 and consequently frees the latter, so that by the leaf springs 52, 53 it can be positioned in the indicated central position. The motor can be driven in both directions and it is moved against a stop 90° relative to the central position. In these 90° end positions, the disk 58 presses against the corresponding side wall of the slot 59 and therefore correspondingly displaces the support 51 of the groove grating 13.

FIG. 5 shows a view where the support 51 has been slightly upwardly displaced and as a result three very accurate positions for the support 51 and therefore the groove grating 13 are obtained.

Alternatively, the drive can take place by means of an electromagnet subject to different voltages, the groove grating being kept in place once again by leaf springs.

FIG. 6 shows moiré line photographs, as can be directly observed on a screen connected to the camera 28. For processing and therefore calculating the positions of the particular points on the surface of the stump, the intensities of the three measurements can be used.

Figure 7:
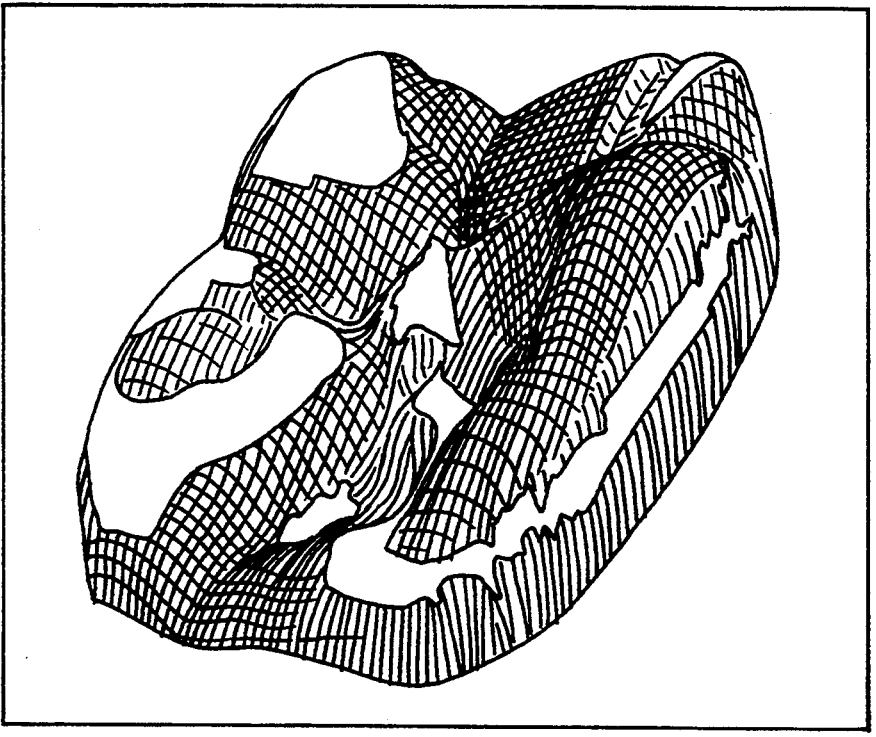
FIG. 7 a view of the contour of the photographed tooth calculated on the basis of the photographs of FIG. 6.

FIG. 7 shows the contour of a tooth calculated on the basis of the moiré photograph and which is similar to what is shown in FIG. 1. On the basis of the data calculated from the moiré photograph or image, it is possible in the same way to control a multi-spindle milling machine for producing the dental prosthesis.

We claim

1. A method for producing a fitting member, the method comprising the steps of repeatedly projecting an optical groove grating in a slightly offset manner onto a reception part for the fitting member, photographing the reception part, and calculating the fitting member on the basis of the photographs, wherein the photographs of the optical groove grating projected onto the reception part are taken by a matrix camera for producing moiré fringes.

2. A method according to claim 1, wherein the matrix camera is a CCD camera.

3. A method according to claim 1, wherein, for the repeated taking of photographs, further comprising the step of displacing the optical groove grating so as to provide an offset with an offset component perpendicular to an extension direction of grooves of the optical groove grating to thereby enable a respective taking of photographs.

4. A method according to claim 3, wherein, for offset purposes, the optical grating is displaced against grating lines thereof by a small displacement angle not equal to 0°.

5. A method according to claim 4, wherein a displacement angle of the grating lines is between 0.1° and 1°.

6. A method according to claim 4, wherein the optical groove grating is displaced by a motor.

7. A method according to claim 4, wherein the optical groove grating is displaced magnetically.

8. A method according to claim 7, wherein the displacement of the optical groove grating is effected by applying discrete different voltages.

9. A method according to claim 4, wherein the optical groove grating is displaced between limiting stops.

10. A method according to one of the claims 4 to 9, wherein the optical grating is maintained in a zero position by springs relieved in the zero position.

11. A method according to claim 1, wherein the lines of the optical grating are optically oriented against columns of the matrix camera at an angle of 90°.

12. A method according to claim 1, wherein the photographs of the optical grating projected onto the reception part are taken in an interlaced mode, and wherein, in each case, photographic frames are taken from the column of uneven or even numbering of the matrix camera.

13. A method according to claim 12, wherein both frames taken in each position of the projected optical grating are compared with one another for generating measuring data.

14. A method for producing a fitting member according to claim 1, wherein the fitting member is a dental prosthesis.

15. A method according to one of claims 1 or 14, wherein the reception part is a remaining stump.

16. An apparatus for manufacturing a fitting member, the apparatus comprising an optical groove grating and an illumination system for enabling repeated projection of the groove grating onto a reception part for the fitting member, and a camera for photographing lines of the optical groove grating projected onto the reception part, wherein an optical deflecting device is disposed between the optical groove grating and the reception part for separating an illuminating beam path impinging through the optical groove grating and an output beam path from the reception part and photographed by the camera, and wherein the camera is a matrix camera for producing moiré fringes.

17. An apparatus according to claim 16, wherein the matrix camera is a CCD camera.

18. An apparatus according to claim 16, wherein a double diaphragm is provided between the illuminating device with the optical groove grating and the camera and the reception part said double diaphragm including closely juxtaposed diaphragm apertures, and wherein deflective optics are provided upstream of at least one of the diaphragm apertures on a side of the double diaphragm remote from the reception part.

19. An apparatus according to claim 16, wherein the optical groove grating is displaceable in a direction perpendicular to an extension direction of groove lines thereof.

20. An apparatus according to claim 19, wherein a device is provided for enabling an offsetting of the optical groove grating at a small angle not equal to 0° with respect to the extension direction of groove lines of the optical groove grating.

21. An apparatus according to claim 20, wherein said device for enabling the offsetting of the optical groove grating is adapted to bring about an offset in an angular range of 0.1 to 1°.

22. An apparatus according to one of claims 20 or 21, wherein the device for enabling the offsetting of the optical groove grating includes a motor.

23. An apparatus according to claim 20, wherein stops are provided for limiting the offsetting of the optical groove grating.

24. An apparatus according to claim 19, wherein the optical groove grating is held in a first or zero position by springs.

25. An apparatus according to claim 16, wherein lines of the matrix camera are oriented optically by 90° against lines of the optical grating.

26. An apparatus according to claim 16, wherein the matrix camera has an interlaced mode for photographing lines of the optical groove grating projected onto the reception part.

27. An apparatus according to claim 26, wherein a device is provided for comparing frames photographed by said matrix camera.

28. An apparatus according to claim 16, wherein the fitting member is a dental prosthesis.

29. An apparatus according to one of claims 16 or 28, wherein the reception part is a remaining stump.

* * * * *